(12) United States Patent
Luo

(10) Patent No.: US 12,110,273 B2
(45) Date of Patent: Oct. 8, 2024

(54) METHOD OF PREPARING INDOLIN-2-ONE COMPOUND AND METHOD OF USING INDOLIN-2-ONE

(71) Applicant: Hefei University of Technology, AnHui (CN)

(72) Inventor: Mei Luo, AnHui (CN)

(73) Assignee: HEFEI UNIVERSITY OF TECHNOLOGY, Anhui (CN)

( * ) Notice: Subject to any disclaimer, the term of this patent is extended or adjusted under 35 U.S.C. 154(b) by 0 days.

(21) Appl. No.: 18/178,765

(22) Filed: Mar. 6, 2023

(65) Prior Publication Data

US 2024/0043383 A1    Feb. 8, 2024

(30) Foreign Application Priority Data

Jul. 26, 2022    (CN) .......................... 202210885083.1

(51) Int. Cl.
   *B01J 31/02*    (2006.01)
   *B01J 37/00*    (2006.01)
   (Continued)

(52) U.S. Cl.
   CPC ........ *C07D 209/40* (2013.01); *B01J 31/0271* (2013.01); *B01J 37/009* (2013.01);
   (Continued)

(58) Field of Classification Search
   CPC ... C07D 209/40; B01J 31/0271; B01J 37/009; B01J 37/04; B01J 2231/34; B01J 2531/002; C07C 253/00; C07B 2200/13
   See application file for complete search history.

(56) References Cited

PUBLICATIONS

Khubeiz, M.J. Synthesis and Spectroscopic Studies on the new Schiff Base Derived from the 1:1 condensation of Isatin with Amines and its Evaluating biological activity Int Journal of ChemTech Res (2016), 516-522. (Year: 2016).*

* cited by examiner

*Primary Examiner* — Mark L Shibuya
*Assistant Examiner* — Kevin S Martin
(74) *Attorney, Agent, or Firm* — Muncy, Geissler, Olds & Lowe, P.C.

(57) ABSTRACT

A compound, having a structure represented by a formula (I),

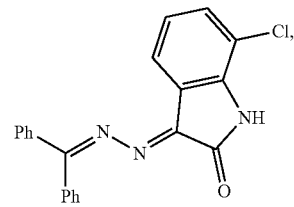

and prepared by one-pot synthesis of benzophenone hydrazone, 7-chloroisatin, and copper(II) acetate monohydrate, and refluxing in 100 mL of anhydrous methanol solvent for 48 hrs. A method for preparing the compound includes: collecting and placing 0.0235 g of benzophenone hydrazone, 0.6914 g of 7-chloroisatin, and 0.6720 g of copper(II) acetate monohydrate complex in a 100.0 mL flask; adding 50 mL of anhydrous methanol as a solvent; stirring a resulting mixture at room temperature for 48 hrs; performing column chromatography separation, and elution with petroleum ether/dichloromethane in a volume ratio of 1:1, and collecting final component points and naturally volatilizing (Continued)

the final component points to obtain 7(E)-chloro-3-diphenylmethylindolin-2-one crystals. The compound is used as a catalyst for reaction between benzophenone imine and trimethylsilonitrile, and has a catalytic effect with a conversion rate reaching 99%.

3 Claims, 1 Drawing Sheet

(51) Int. Cl.
*B01J 37/04* (2006.01)
*C07C 253/00* (2006.01)
*C07D 209/40* (2006.01)
(52) U.S. Cl.
CPC ............. *B01J 37/04* (2013.01); *C07C 253/00* (2013.01); *B01J 2231/34* (2013.01); *B01J 2531/002* (2013.01); *C07B 2200/13* (2013.01)

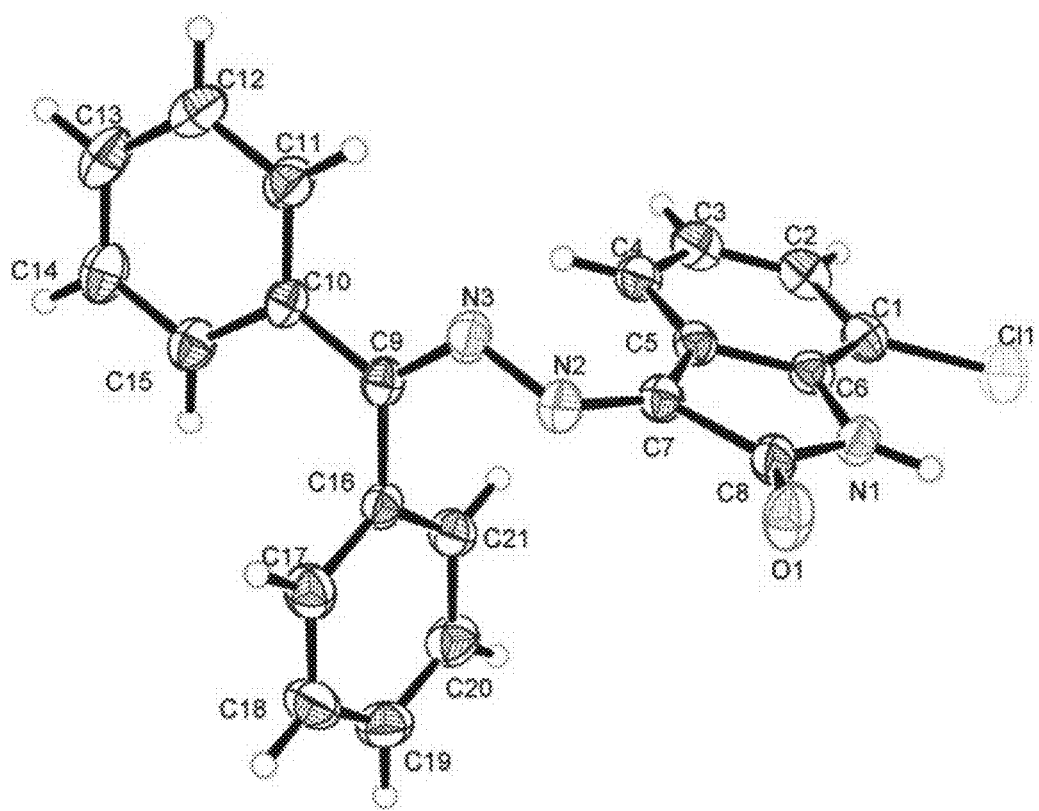

METHOD OF PREPARING INDOLIN-2-ONE COMPOUND AND METHOD OF USING INDOLIN-2-ONE

CROSS-REFERENCE TO RELATED APPLICATIONS

Pursuant to 35 U.S.C. § 119 and the Paris Convention, this application claims the benefit of Chinese Patent Application No. 202210885083.1 filed Jul. 26, 2022, the contents of which are incorporated herein by reference.

BACKGROUND

Technical Field

The present application relates to use of a compound, and more particularly to a preparation method and a use of indolin-2-one, and specifically relates to a preparation method and a use of 7(E)-chloro-3-diphenylmethyleneindolin-2-one.

Description of the Related Art

The statements herein only provide background information related to the present application, and do not necessarily constitute prior art.

Indolin-2-one compounds are important pharmaceutical intermediates, and have extremely wide use. Similar synthesis methods and applications of indolin-2-one compounds have been reported [1].

[1] Reference: Synthesis and spectroscopic studies on the new Schiff base derived from the 1:1 condensation of isatin with amines and its evaluating biological activity, Khubeiz, Mohamad Jawad, International Journal of ChemTech Research (2016), 9(7), 516-522.

SUMMARY

The compound referred to in the present application is a compound having a structure represented by a formula (I) and prepared by one-pot synthesis of benzophenone hydrazone, 7-chloroisatin, and copper(II) acetate monohydrate, and refluxing in 100 mL of anhydrous methanol solvent for 48 hrs:

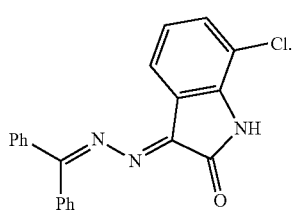

(I)

Chemical name: 7(E)-chloro-3-benzophenone hydrazone 2-indanone

Common name: benzophenone-7-chloroisatin azine

The compound having the structure represented by formula (I) is synthesized as follows: 0.0235 g of benzophenone hydrazone, 0.6914 g of 7-chloroisatin, and 0.6720 g of copper(II) acetate monohydrate complex are collected and placed in a 100.0 mL flask, in which 50 mL of anhydrous methanol is added as a solvent, a resulting mixture is stirred at room temperature for 48 hrs, column chromatography separation is performed, and elution is performed with petroleum ether/dichloromethane (a volume ratio of 1/1), and final component points collected are naturally volatilized to obtain 7 (E)-chloro-3-diphenylmethylindolin-2-one crystals.

The reaction mechanism of this reaction is speculated as follows: benzophenone hydrazone, under the action of copper salt, first dimerizes to form benzophenone azine, a dimeric intermediate of benzophenone hydrazone, and then reacts with 7-chloroisatin to form the target product in one step.

The target product showed good catalytic performance in the nitrile silylation reaction of benzophenone imine, with a conversion rate reaching 99%.

BRIEF DESCRIPTION OF THE DRAWINGS

The sole figure is a single crystal diffraction pattern of the target product benzophenone-7-chloroisatin azine.

DETAILED DESCRIPTION OF THE EMBODIMENTS

To further illustrate the present application, experiments detailing preparation and use of (E)-chloro-3-diphenylmethyleneindolin-2-one are described below. It should be noted that the following examples are intended to describe and not to limit the present application.

Example 1. Preparation of (E)-chloro-3-diphenylmethyleneindolin-2-one

Under an anhydrous and anaerobic condition, 0.0235 g of benzophenone hydrazone, 1.0 g of 7-chloroisatin, and 0.6720 g of copper (II) acetate monohydrate complex were collected and added into a 100 mL two-mouth flask. 50 mL anhydrous methanol was added as a solvent, and stirred at room temperature for 48 hrs. Column chromatography separation was performed, petroleum ether/dichloromethane (having a volume ratio of 1/1) was used for elusion, and final component points were collected and naturally volatilized to obtain 7(E)-chloro-3-diphenylmethyleneindolin-2-one crystals, which have a yield of 82%; red-brown crystals, and a melting point>200° C.; 1H NMR (500 MHZ, 298K, CDCl3) δ ppm 10.9(s, 1H) 7.76-7.78 (m, 2H, ArH), 7.62 (d, J-7.5 Hz, ArH), 7.41-7.54 (m, 7H),7.41 (d, J-8.2 Hz, 1H), 7.19(d, J-7.3 Hz, 1H), 13C{1H} NMR (125 MHZ, 298K, CDCl3)164.6, 158.5, 146.2, 142.0, 138.1, 136.5, 134.0, 132.8, 130.8, 129.9, 129.2(x2), 129.0(x2), 128.6 (x2), 128.2(x2), 125.9, 123.5, 118.5, 115.9; HRMS (EI) m/z (%) calcd for $C_{21}H_{14}N_3OCl$ 360.0896; found: 359.8130; $V_{max}$ ($cm^{-1}$) 3084, 1725, 1615, 1583, 1475, 1442, 1432, 1400, 1317, 1328, 1317, 1299, 1222, 1170, 1137, 1072, 1031, 1072, 1009, 1000, 948, 931, 910, 836, 796, 796, 766, 757, 732, 664, 652, 593, 558;

Data of nitrogen compound crystal data are as follows:

| | |
|---|---|
| Empirical formula | C21H14N3OCl |
| Molecular weight | 359.80 |
| Temperature | 293(2) K. |
| wavelength | 1.54184 Å |
| Crystal system, space group | Monoclinic, I2/a |
| Unit cell dimensions | a = 16.9274(3) Å  α = 90°. |
| | b = 10.18017(18) Å  β = 99.926 (2)°. |
| | c = 20.2755(4) Å  γ = 90° |

TABLE 1-continued

| | |
|---|---|
| volume | 3441.64 (11) Å³ |
| charge density | 8, 1.389 Mg/m³ |
| Absorption correction parameter | 2.083 mm⁻¹ |
| Number of electrons in a unit cell | 252 |
| Crystal size | 0.22 × 0.18 × 0.15 mm |
| Theta range | 8.856 to 145.756 |
| Collection range of | $-20 \le h \le 20$, |
| HKL's indicator | $-11 < k \le 12$, |
| | $-18 < l \le 24$ |
| Reflections collected/unique | 6937/3338[R(int) = 0.0228] |
| Absorption correction method | Multi-layer scanning |
| Refinement method | Full-matrix least-square on F² |
| Data number/restraint number/parameter number | 3338/0/235 |
| Refinement method | 1.047 |
| Uniformity factor of diffraction point | $R_1 = 0.0358, wR_2 = 0.0929$ |
| Observable diffraction fit factor | $R_1 = 0.0416, wR_2 = 0.0997$ |
| Largest peak and hole on the difference Fourier diagram | 0.17 and −0.23 e.Å⁻³ |

TABLE 2

Typical bond length data of crystal

| Atom | Atom | Length/Å | Atom | Atom | Length/Å |
|---|---|---|---|---|---|
| C11 | C1 | 1.7267(16) | C7 | C8 | 1.5094(18) |
| O1 | C8 | 1.2213(17) | C10 | C15 | 1.391(2) |
| N1 | C6 | 1.3971(17) | C10 | C11 | 1.403(2) |
| N1 | C8 | 1.3613(19) | C4 | C3 | 1.388(2) |
| N2 | N3 | 1.3568(17) | C15 | C14 | 1.383(2) |
| N2 | C7 | 1.2836(19) | C11 | C12 | 1.379(2) |
| N3 | C9 | 1.2832(18) | C21 | C20 | 1.388(2) |
| C9 | C16 | 1.4940(19) | C1 | C2 | 1.397(2) |
| C9 | C10 | 1.4777(19) | C2 | C3 | 1.378(3) |
| C5 | C6 | 1.403(2) | C17 | C18 | 1.389(3) |
| C5 | C7 | 1.457(2) | C20 | C19 | 1.367(3) |

TABLE 4

Bond Lengths for lm-12-yellow_autored.

| Atom | Atom | Length/Å | Atom | Atom | Length/Å |
|---|---|---|---|---|---|
| C5 | C4 | 1.3938(19) | C12 | C13 | 1.381(3) |
| C6 | C1 | 1.376(2) | C18 | C19 | 1.382(3) |
| C16 | C21 | 1.388(2) | C13 | C14 | 1.376(3) |
| C16 | C17 | 1.385(2) | | | |

TABLE 3

Typical bond length data of crystal

| Atom | Atom | Atom | Angle/° | Atom | Atom | Atom | Angle/° |
|---|---|---|---|---|---|---|---|
| C8 | N1 | C6 | 111.02(12) | C11 | C10 | C9 | 120.67(13) |
| C7 | N2 | N3 | 117.42(13) | O1 | C8 | N1 | 126.47(13) |
| C9 | N3 | N2 | 121.83(12) | O1 | C8 | C7 | 127.57(14) |
| N3 | C9 | C16 | 122.71(13) | N1 | C8 | C7 | 105.95(12) |
| N3 | C9 | C10 | 116.86(13) | C3 | C4 | C5 | 118.23(15) |
| C10 | C9 | C16 | 120.39(12) | C14 | C15 | C10 | 120.54(16) |
| C6 | C5 | C7 | 105.88(12) | C12 | C11 | C10 | 120.38(15) |
| C4 | C5 | C6 | 120.23(14) | C16 | C21 | C20 | 120.49(16) |
| C4 | C5 | C7 | 133.90(14) | C6 | C1 | C11 | 119.98(12) |
| N1 | C6 | C5 | 110.52(12) | C6 | C1 | C2 | 118.56(14) |

TABLE 5

Bond Angles for lm-12-yellow_autored.

| Atom | Atom | Atom | Angle/° | Atom | Atom | Atom | Angle/° |
|---|---|---|---|---|---|---|---|
| C1 | C6 | N1 | 128.51(14) | C2 | C1 | C11 | 121.45(12) |
| C1 | C6 | C5 | 120.97(13) | C3 | C2 | C1 | 120.59(15) |
| C21 | C16 | C9 | 119.13(13) | C16 | C17 | C18 | 120.06(16) |
| C17 | C16 | C9 | 121.70(13) | C2 | C3 | C4 | 121.41(14) |
| C17 | C16 | C21 | 119.17(14) | C19 | C20 | C21 | 119.99(17) |
| N2 | C7 | C5 | 133.56(13) | C11 | C12 | C13 | 120.40(16) |
| N2 | C7 | C8 | 119.90(13) | C19 | C18 | C17 | 120.05(17) |
| C5 | C7 | C8 | 106.53(12) | C20 | C19 | C18 | 120.24(16) |
| C15 | C10 | C9 | 120.90(13) | C14 | C13 | C12 | 119.73(16) |
| C15 | C10 | C11 | 118.43(14) | C13 | C14 | C15 | 120.52(16) |

Example 2. Use of target compound (I) in nitrile silylation reaction of benzophenone imine

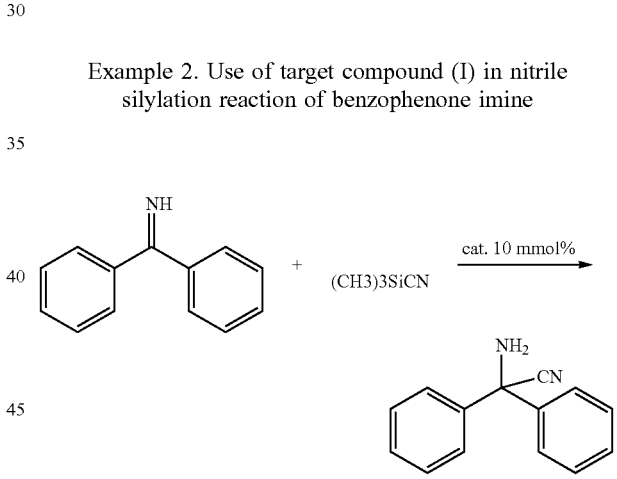

0.1 mmol of a complex was collected and added into a 25 mL small flask, 2 mL of anhydrous methanol was added, then 1.0 mmol of benzophenone imine and 0.3 mL of trimethylsilonitrile were added to the solution, and stirred at room temperature for 15 hrs. After that, 1HNMR detection was performed, and a catalytic conversion was 75%. 1H NMR (600 MHz, CDCl3, 27° C.) δ 7.23-7.59 (m, 10H), 4.10 (s, 2H).

Unless otherwise indicated, the numerical ranges involved in the present application include the end values. While particular embodiments of the present application have been shown and described, it will be obvious to those skilled in the art that changes and modifications may be made without departing from the present application in its broader aspects, and therefore, the aim in the appended claims is to cover all such changes and modifications as fall within the true spirit and scope of the present application.

What is claimed is:

1. A compound, having a structure represented by a formula (I),

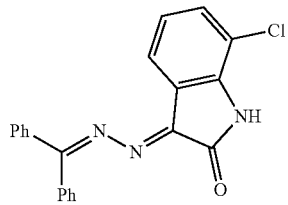

(I)

and prepared by one-pot synthesis of benzophenone hydrazone, 7-chloroisatin, and copper(II) acetate monohydrate, and refluxing in 100 mL of anhydrous methanol solvent for 48 hrs.

2. The compound of claim 1, prepared into a form of a crystal, wherein when being diffracted with a CuKα ray, which is monochromated by a graphite monochromator and has a wavelength of λ=1.54184 Å on an Oxford X-ray single crystal diffractometer at a temperature of 293(2)K, the crystal of the compound belongs to a monoclinic system, I2/a, and has cell parameters as follows: a=16.9274(3) Å, alpha=90 deg; b=10.18017(18) Å, beta=99.926(2) deg; c=20.2755(4) Å, gamma=90 deg.

3. A method for preparing a compound having a structure represented by a formula (I),

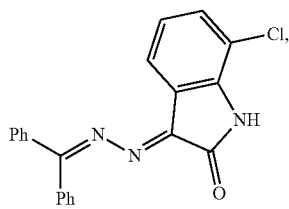

(I)

the method comprising:
collecting and placing 0.0235 g of benzophenone hydrazone, 0.6914 g of 7-chloroisatin, and 0.6720 g of copper(II) acetate monohydrate complex in a 100.0 mL flask;
adding 50 mL of anhydrous methanol as a solvent;
stirring a resulting mixture at room temperature for 48 hrs;
performing column chromatography separation, and elution with petroleum ether/dichloromethane in a volume ratio of 1:1; and
collecting final component points and naturally volatilizing the final component points to obtain 7(E)-chloro-3-diphenylmethylindolin-2-one crystals.

* * * * *